United States Patent [19]
Sim

[11] Patent Number: 6,099,867
[45] Date of Patent: Aug. 8, 2000

[54] NUTRACEUTICAL ANTLER POWDER AND A METHOD OF PRODUCING SAME

[76] Inventor: Jeong S. Sim, 6508-127 Street, Edmonton, Alberta, Canada, T6H 3X1

[21] Appl. No.: 09/105,664

[22] Filed: Jun. 26, 1998

Related U.S. Application Data

[60] Provisional application No. 60/050,799, Jun. 26, 1997.

[51] Int. Cl.⁷ .................................................. A61K 35/32
[52] U.S. Cl. ............................................ 424/549; 424/543
[58] Field of Search ..................................... 424/520, 543, 424/549; 426/43, 61; 530/413

[56] References Cited

U.S. PATENT DOCUMENTS

| | | | |
|---|---|---|---|
| 4,702,923 | 10/1987 | Tokumaru et al. ....................... | 426/61 |
| 4,797,290 | 1/1989 | Tokumaru et al. ....................... | 426/43 |
| 5,408,041 | 4/1995 | Mundy et al. ........................... | 530/413 |

FOREIGN PATENT DOCUMENTS

| | | | |
|---|---|---|---|
| 9201557 | 2/1992 | Rep. of Korea ................. | A23L 1/29 |
| 207787 | 4/1997 | Russian Federation ....... | A61K 35/32 |

*Primary Examiner*—Jean C. Witz
*Assistant Examiner*—Angela N. Trafton
*Attorney, Agent, or Firm*—Emery Jamieson

[57] ABSTRACT

A nutraceutical composition comprising water insoluble antler powder or water soluble antler powder or a combination of both. Also disclosed is a method of producing antler powder, either water soluble, water insoluble or a combination of both.

6 Claims, 1 Drawing Sheet

6,099,867

NUTRACEUTICAL ANTLER POWDER AND A METHOD OF PRODUCING SAME

This application claims benefit of U.S. Provisional Application No. 60/050,799, filed Jun. 26, 1997.

FIELD OF THE INVENTION

The invention relates to antler powder, a process for the production of the same and a nutraceuticals which contain the same.

BACKGROUND TO THE INVENTION

Antlers or horns from such animals as elk, deer, reindeer or caribou have long been recognized by many cultures to have medicinal or tonic effect. Extracts of such antlers, when ingested by humans, are said to lower blood pressure, fight aging, promote natural healing processes, reduce inflammation, boost the immune system and vitality and enhance sexual desire.

Traditionally, antlers have been harvested while they are rapidly growing as it is believed that the medicinal ingredients are most concentrated at that time. However, antlers are naturally shed once a year and it would be advantageous to derive extracts from the dead antlers.

Known methods of producing a suitable product from antlers include air-drying and grinding. In this method, the antlers are thinly sliced and then dried at over 60° C. for 40 days or more. The resulting slices are then ground up to produce antler powder. This method is disadvantageous because it is inefficient and time consuming. The resulting powder may be contaminated by human pathogens or hair and may also have an unpleasant odor or texture which may make the powder unsuitable for human food use. More importantly, the composition of the powder is inconsistent and unpredictable.

Other known methods of producing antler products involve extractions of pulverized antler with ethanol or water or both, followed by freeze-drying of the extract. The pulverization process is more easily performed if the antlers are frozen, preferably with liquid nitrogen. However, it is likely that significant amounts of medicinal ingredients remain bound up in the insoluble antler matrix after extraction and it would be desirable to include those ingredients in the end product.

There remains a need in the art for a controllable and hygienic process to extract both soluble and insoluble ingredients from antlers harvested at any time during the antler growth cycle which process results in a consistent end product which is substantially free of hair and pathogenic contamination and which is otherwise suitable for human food use.

SUMMARY OF THE INVENTION

In accordance with one aspect of the invention, the invention is a method of producing a combination of water soluble and insoluble antler powder, said method comprising:

(a) retorting whole antler segments comprising skin and hard tissue at a temperature in the range of about 100° C. to about 120° C.;

(b) separating the skin from the hard tissue;

(c) homogenizing the skin and the hard tissue separately;

(d) filtering the skin homogenate to remove and discard any hairs;

(e) combining the skin and tissue homogenates;

(f) separating the combined homogenate into aqueous and solid fractions;

(g) lyophilizing the aqueous fraction and the solid fraction separately;

(h) pulverizing the lyophilized aqueous fraction to form water soluble antler powder;

(i) pulverizing the lyophilized solid fraction to form water insoluble antler powder; and (j) combining the water soluble powder and the water insoluble powder to form whole antler powder.

In accordance with another aspect of the invention, the invention is a method of producing a combination of water soluble and insoluble antler powder, said method comprising;

(a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the aqueous fraction and the solid fraction separately;

(e) pulverizing the lyophilized aqueous fraction to form water soluble antler powder;

(f) pulverizing the lyophilized solid fraction to form water insoluble antler powder; and (g) combining the soluble antler powder and the insoluble antler powder to form whole antler powder.

In a third aspect of the invention, the invention comprises a method of producing water soluble antler powder comprising the steps of:

(a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the aqueous fraction; and (e) pulverizing the lyophilized aqueous fraction to form water soluble antler powder.

In a fourth aspect of the invention, the invention is a method of producing water insoluable antler powder comprising the steps of:

(a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the solid fraction; and (e) pulverizing the lyophilized solid fraction to form water insoluble antler powder.

BRIEF DESCRIPTION OF THE DRAWING

The sole appended FIGURE is a flow diagram of a process for the production of antler powder of the present invention.

DETAILED DESCRIPTION OF THE PREFERRED EMBODIMENT

Figure 1:
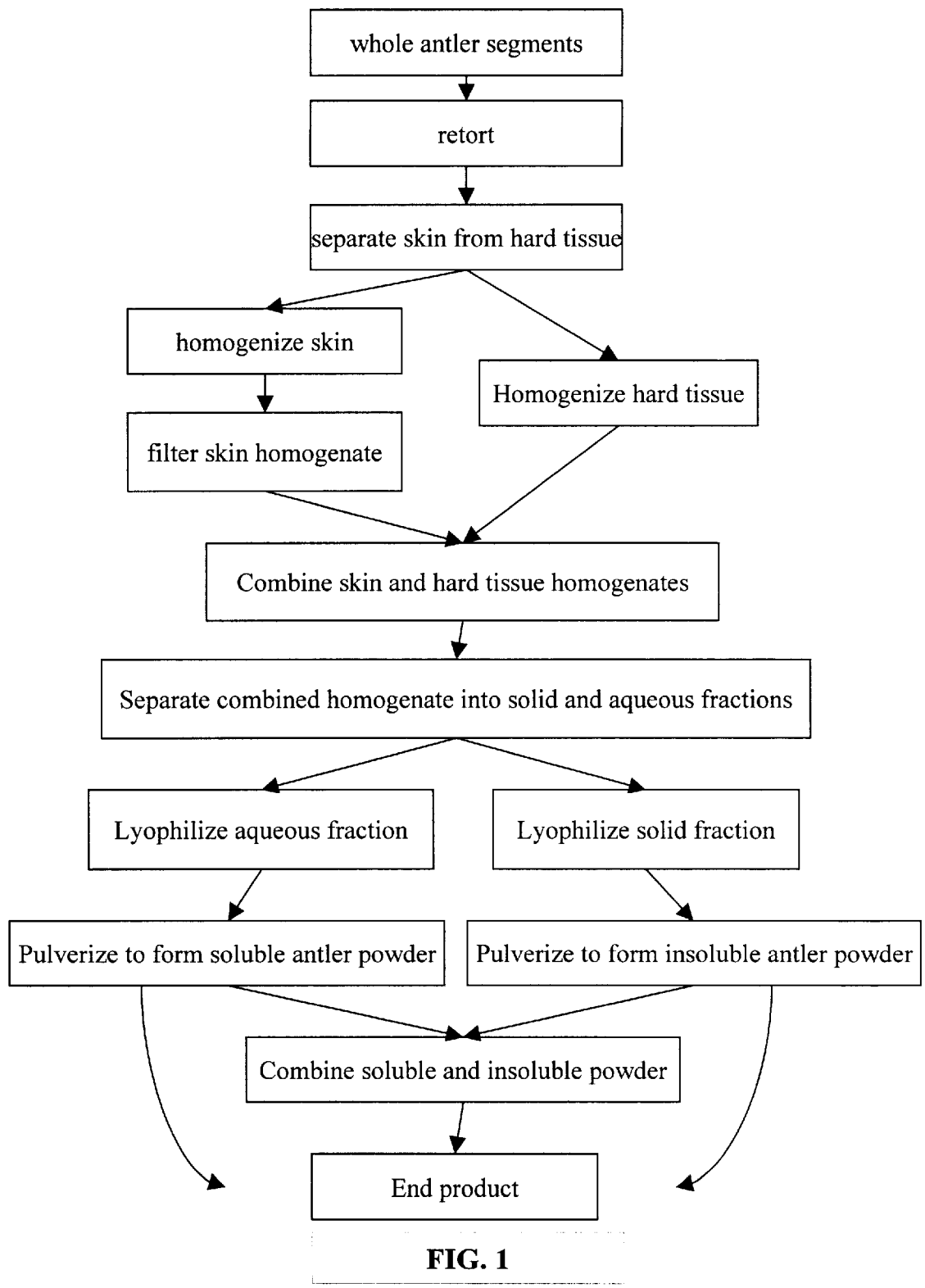

The present invention is directed to antler powder produced by a method as described herein and nutraceutical compositions containing such powder. The antlers are those grown by species of elk, deer, reindeer or caribou or similar animals.

In this specification and in the claims, "nutraceutical" shall mean a food or food component that is intended to promote health. Such food or food components contain sources that are indicated to be epidemiologically important in disease prevention and have been shown to be likely to help prevent chronic diseases.

The method described as the preferred embodiment is described in reference to manual operations, however, it will be readily apparent to one skilled in the art that any or all of the steps of the within described method may be automated. The method is equally applicable to antlers harvested during their growth phase or antlers harvested later in the growth cycle, even antlers which have been shed by the animal at the end of the cycle.

In general, the method begins with fresh or frozen antlers which are comprised of an outer skin layer and an inner hard tissue core. The antlers are cut to a convenient length by any suitable means. If frozen, the antlers may be thawed to room temperature. It is preferable that the antler be first washed with a soft brush and warm water to remove any extraneous or foreign material before further treatment. The antler pieces are then retorted for approximately 2 hours at a temperature in the range of about 100° C. to about 120° C. at a pressure of approximately 15 p.s.i. More severe retort conditions may be required if the antlers display a high degree of calcification.

In the preferred embodiment, after retorting, the skin is removed and separated from the hard tissue for separate processing. Distilled water is then added to the hard tissue fraction to achieve approximately 2:1 ratio of water to hard tissue by weight. The hard tissue is then homogenized by blending at high speed for approximately 5 minutes in a Waring blender.

Distilled water is also added to the skin fraction again in a 2:1 ratio. The skin is also homogenized by high speed blending. The skin fraction contains undesirable hairs and should be filtered to remove the hair contamination. The homogenized skin fraction is passed through four layers of cheese cloth twice to remove hair contamination. The filtrate is washed with small amounts of distilled water.

The hard tissue and skin homogenates are then combined and re-homogenized by high speed blending. The resulting combined homogenate is then separated into solid and liquid fractions. The preferable method for such separation is low speed centrifugation. Alternatively, the combined homogenate may be filtered to achieve such separation.

The precipitate is then lyophilized and pulverized to a suitable mesh size. The supernate from the centrifugation step is also lyophilized, leaving a solid residue which is also pulverized to a desired mesh size.

The residue from the lyophilized supernate comprises primarily water soluble antler powder while the lyophilized precipitate comprises primarily water insoluble antler powder. The soluble and insoluble powders may be combined to form whole antler powder or may be used separately for different purposes. The soluble antler powder contains the bulk of the proteinaceous material while the insoluble antler powder is a richer source of minerals.

Either the soluble powder or the insoluble powder, or preferably the combined whole antler powder, may be used to form nutraceutical capsules or tablets or may be used as an ingredient in nutritional bars, beverages or the like. The soluble antler powder is suitable for preparation of a tonic beverage. The insoluble antler powder may be used as a mineral supplement in a wide variety of different forms.

The following example is an illustration of the preferred embodiment and is not intended to limit the invention in any way.

EXAMPLE 1

Frozen elk antlers were cut to 30 cm lengths by an electric chain saw. The antler pieces were gently washed with clean warm water and a soft brush and then retorted for 2 hours at 120° C. at 15 p.s.i The skin was then removed by hand and kept separate from the hard tissue.

The skin was homogenized for 5 minutes at high speed in a Waring blender. The skin homogenate was then filtered twice through four layers of cheese cloth and the filtrate was washed with a small amount of distilled water.

The hard tissue was also homogenized for 5 minutes at high speed in a Waring blender. The hard tissue homogenate is then added to the filtered skin homogenate and the mixture was re-homogenized for an additional 5 minutes.

The combined homogenate was then centrifuged at approximately 1000×g for 15 minutes. Both the precipitate portion and the supernate portion were separately lyophilized, and the resulting solids from each portion separately pulverized with a grinder to a fine powder. The soluble and insoluble antler powders were then combined to form whole antler powder. Yield mass of whole antler powder was approximately 30% of the antlers used in the process.

The whole, soluble and insoluble antler powder were each analyzed for chemical-physical properties with the following results:

TABLE 1

Chemical Composition for Antler Products

| Antler | Proximate Analysis (% of total mass) | | | | |
|---|---|---|---|---|---|
|  | Moisture | Protein | Lipids | NFE + Fibre | Ash |
| Whole | 0.6 | 62.8 | 0.5 | 0.5 | 35.1 |
| Soluble | 20.3 | 80.6 | 0.8 | 0.6 | 5.0 |
| Insoluble | 1.9 | 33.6 | 1.9 | 2.9 | 63.6 |

| Antler | Macro Minerals (% of total mass) | | | | |
|---|---|---|---|---|---|
|  | Ca | P | K | Na | S | Mg |
| Whole | 13.27 | 6.54 | 0.25 | 0.80 | 0.45 | 0.39 |
| Soluble | 0.59 | 0.38 | 0.49 | 0.84 | — | 0.04 |
| Insoluble | 25.64 | 11.86 | 0.08 | 0.51 | — | 0.46 |

The proximate analysis was performed in accordance with the Official Methods of Analysis, AOCS (Association of Official Analytical Chemists), 14th ed., Washington D.C., 1987. The Micro Kjeldahl method was used for protein determination; the ether Soxhlet extract method for lipid determination; furnace decomposition method for ash determination; and moisture content determined by the oven dry method. NFE (nitrogen-free extract) plus fibre is computed as 100%−(% protein+% lipid+% ash+% moisture). Mineral analysis was done by emission spectrographic methods.

The embodiments of the invention in which an exclusive property and privilege are claimed are as follows:

1. A method of producing a combination of water soluble and insoluble antler powder, said method comprising:
   (a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the aqueous fraction and the solid fraction separately;

(e) pulverizing the lyophilized aqueous fraction to form water soluble antler powder;

(f) pulverizing the lyophilized solid fraction to form water insoluble antler powder; and (g) combining the soluble antler powder and the insoluble antler powder to form whole antler powder.

2. The method of claim 1 further comprising the steps of separating the skin from the hard tissue, homogenizing the skin and the hard tissue separately, filtering the skin homogenate to remove and discard any hairs and combining the skin and tissue homogenates.

3. A method of producing water soluble antler powder, said method comprising:

(a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the aqueous fraction; and (e) pulverizing the lyophilized aqueous fraction to form water soluble antler powder.

4. The method of claim 3 wherein the antler segment homogenization step further comprises the steps of separating the skin from the hard tissue, homogenizing the skin and hard tissue separately, filtering the skin homogenate to remove and discard any hairs and combining the skin and tissue homogenates.

5. A method of producing water insoluble antler powder, said method comprising:

(a) retorting whole antler segments comprising skin, hair and hard tissue at a temperature in the range of about 100° C. to about 120° C.;

(b) homogenizing the antler segments;

(c) separating the homogenate into aqueous and solid fractions;

(d) lyophilizing the solid fraction; and (e) pulverizing the lyophilized solid fraction to form water insoluble antler powder.

6. The method of claim 5 wherein the antler segment homogenization step further comprises the steps of separating the skin from the hard tissue, homogenizing the skin and hard tissue separately, filtering the skin homogenate to remove and discard any hairs and combining the skin and tissue homogenates.

* * * * *